(12) United States Patent
Khan

(10) Patent No.: US 8,747,344 B2
(45) Date of Patent: *Jun. 10, 2014

(54) HYBRID ARTERIOVENOUS SHUNT

(71) Applicant: Nazir A. Khan, Burr Ridge, IL (US)

(72) Inventor: Nazir A. Khan, Burr Ridge, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/645,862

(22) Filed: Oct. 5, 2012

(65) Prior Publication Data

US 2014/0100508 A1    Apr. 10, 2014

Related U.S. Application Data

(63) Continuation of application No. 10/812,380, filed on Mar. 29, 2004, now Pat. No. 8,282,591.

(51) Int. Cl.
*A61B 19/00*    (2006.01)

(52) U.S. Cl.
USPC ............................................................. 604/7

(58) Field of Classification Search
USPC .......... 604/7–10, 6.16, 272, 533, 264, 507–8, 604/271; 210/645, 646, 600, 634; 606/153, 606/167

See application file for complete search history.

(56) References Cited

U.S. PATENT DOCUMENTS

| | | | | |
|---|---|---|---|---|
| 5,509,897 A | * | 4/1996 | Twardowski et al. | 604/43 |
| 5,591,226 A | * | 1/1997 | Trerotola et al. | 623/1.12 |
| 6,102,884 A | * | 8/2000 | Squitieri | 604/8 |
| 8,282,591 B2 | * | 10/2012 | Khan et al. | 604/8 |

* cited by examiner

*Primary Examiner* — Leslie Deak

(57) ABSTRACT

An apparatus for positioning a graft and catheter operable for subcutaneous access to the vascular system of a patient. A surgically created, hybrid arteriovenous shunt is provided which comprises a flexible graft and a venous outflow catheter connected to the graft via surgical anastomosis over a cuff. The graft is connected to an arterial source and then to a single lumen venous outflow catheter which deposits dialyzed blood directly into the heart at the right atrium. Methods of surgical placement and performing hemodialysis using embodiments of the apparatus are provided.

20 Claims, 3 Drawing Sheets

HYBRID ARTERIOVENOUS SHUNT

CROSS-REFERENCE TO RELATED APPLICATIONS

This application is a continuation of U.S. application Ser. No. 10/812,380 filed on Mar. 29, 2004 and entitled Hybrid Arteriovenous Shunt, which is hereby incorporated by reference herein in its entirety.

BACKGROUND OF THE INVENTION

Field of the Invention

Hybrid Arteriovenous Shunt

The present invention relates to devices, systems and methods for subcutaneously positioning a graft and catheter for access to the vascular system of a patient.

The present invention relates to methods and apparatus for subcutaneously positioning a graft and catheter for access to the vascular system of a patient. In particular, this invention relates to an arteriovenous (AV) shunt for use in conjunction with hemodialysis.

Hemodialysis is the purification of blood by removing toxic substances and restoring chemical balance using an extracorporeal dialysis machine. The process is used as a substitute for proper kidney function in those with renal failure. Despite the benefits, a persistent drawback of hemodialysis devices is patient morbidity and mortality caused by failure of and infection from the hemodialysis access site. In particular, nearly 80% of access failure in arteriovenous grafts is caused by blood returning from the hemodialysis machine into the patient with sufficient high pressure to damage vein walls. Morbidity and Mortality of Dialysis, NIH Consens. Statement 1993; 11:1-33.

Hemodialysis access sites include arteriovenous grafts, arteriovenous fistulas and hemodialysis catheters. An arteriovenous graft is a tube surgically placed under the skin, which is connected to an arterial source on one end and a venous source on the other. The graft is accessed by the cannulas of the dialysis machine, so the blood is removed from the body, cleansed in the dialysis filter and then returned to the patient. An AV fistula is a direct connection of an artery to a vein where a graft is not used. The vein is used for dialysis access. A hemodialysis catheter is a percutaneous tube placed through the skin and directly into the subclavian vein, internal jugular vein or femoral vein. The extracutaneous portion is used for dialysis access.

These access methods are problematic because they cause vein damage and leave the patient susceptible to infection and clotting. Furthermore, the weak veins of renal failure patients may not accommodate certain access methods.

In AV grafts, neointimal hyperplasia is caused when the cells of the inner layer of the vein hypertrophy and multiply in response to the high blood flow and pressure of the arteries. This multiplication along with turbulent flow causes frequent venous outflow obstruction and resultant clotting and failure of the AV graft. (Paulson, W. D.; Ram, S. J.; Zibari, G. B., "Vascular Access: Anatomy, Examination, Management", Semin. Nephrol., Vol. 22, No. 3, May 2002, pp. 183-194). In AV fistulas, the common cause of failure is formation of venous aneurysms and clotting on the venous portion of the graft. Venous aneurysms are caused because of the flow pressure differential between the high pressure grafted artery and the vein. High pressure arterial flow through the thin walls of the veins causes damage because veins lack the prominent arterial layers of elastic and muscular tissue. These aneurysms then form clots because of the turbulent, irregular blood flow and subsequently the AV fistula completely clots off and fails. [U.S. Pat. Nos. 6,102,884; 6,086,553; 5,556,426; 4,822,341; 4,654,033; 4,479,798; 3,998,222; 3,826,257; 3,818,257; and 3,818,511—incorporated by reference.] Hemodialysis catheters are the least preferred in the surgical community. The large bore catheters can last from two months to one year and are frequently complicated by infection and clotting because the limbs of the catheters are outside of the skin.

It would be desirable to have an arteriovenous device placed subcutaneously that does not require anastomisis to a vein, eliminates exposure of the vein to high pressure blood returning to the patient from the dialysis apparatus and utilizes a single lumen venous outflow catheter. It would also be desirable to have an arteriovenous device that provides long term patency, prevents clotting and minimizes infection.

SUMMARY

The present invention provides an arteriovenous shunt comprising:

a. an arterial graft comprising a body, a lead end and a terminal end, wherein said lead end is operable for subcutaneous connection to an artery by anastomosis;

b. a single lumen venous outflow catheter comprising an intake end and depositing end, wherein said depositing end is operable for insertion through a vein into the right atrium of the heart; and c. a cuff comprising an inlet and an outlet, wherein:

i. said inlet is connected to said terminal end of said subcutaneous graft; and ii. said outlet is connected to said intake end of said venous outflow catheter.

The present invention also provides a system for performing hemodialysis on a patient comprising:

a. an arteriovenous shunt comprising:

i. an arterial graft comprising a body, a lead end and a terminal end, wherein said lead end is operable for subcutaneous connection to an artery by anastomosis; and ii. a single lumen venous outflow catheter comprising an intake end and a depositing end, wherein said depositing end is operable for insertion through a vein into the right atrium of the heart; and iii. a cuff comprising an inlet and an outlet, wherein:

1. said inlet is connected to said terminal end of said subcutaneous graft; and 2. said outlet is connected to said intake end of said venous outflow catheter; and b. a hemodialysis apparatus.

The present invention additionally provides a method of performing hemodialysis on a patient comprising:

a. inserting an arteriovenous shunt into a patient, wherein said arteriovenous shunt comprises:

i. an arterial graft comprising a body, a lead end and a terminal end, wherein said lead end is operable for subcutaneous connection to an artery by anastomosis;

ii. a single lumen venous outflow catheter comprising an intake end and depositing end, wherein said depositing end is operable for insertion through a vein into the right atrium of the heart; and iii. a cuff comprising an inlet and an outlet, wherein:

1. said inlet is connected to said terminal end of said subcutaneous graft; and 2. said outlet is connected to said intake end of said venous outflow catheter;

b. connecting said arterial graft to a hemodialysis apparatus;

c. collecting blood from the patient through said subcutaneous graft;

d. passing said blood through the hemodialysis apparatus;

e. collecting purified blood from hemodialysis apparatus; and f. transmitting said purified blood through said cuff into said venous outflow catheter.

It has been found that the methods and apparatus of this invention afford benefits over methods and apparatus among those known in the art. Such benefits include one or more of long term patency, prevention of clotting and minimizing infection. Further benefits and embodiments of the present invention are apparent from the description set forth herein.

BRIEF DESCRIPTION OF THE DRAWINGS

The present invention will become more fully understood from the detailed description and the accompanying drawings, wherein.

Figure 1:
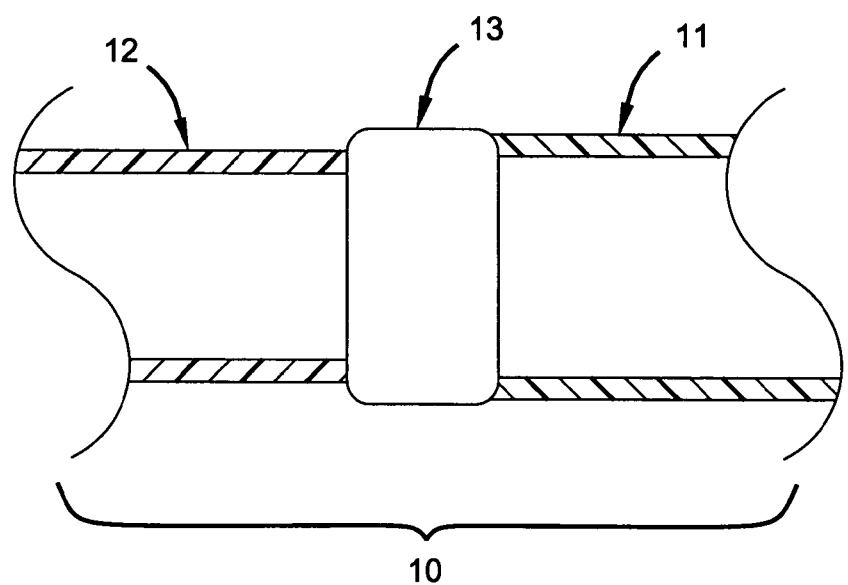
FIG. 1 depicts the segments of an arteriovenous shunt of the present invention.

It should be noted that the figures set forth herein are intended to exemplify the general characteristics of an apparatus, materials and methods among those of this invention, for the purpose of the description of such embodiments herein. These figures may not precisely reflect the characteristics of any given embodiment, and are not necessarily intended to define or limit specific embodiments within the scope of this invention.

DETAILED DESCRIPTION OF THE INVENTION

While this invention is susceptible of embodiments in many different forms, there are shown in the drawings and will herein be described in detail, preferred embodiments of the invention with the understanding that the present disclosure is to be considered as an exemplification of the principles of the invention and is not intended to limit the broad aspect of the invention to the embodiments illustrated.

The present invention provides devices, systems and methods for subcutaneously positioning a graft and catheter for access to the vascular system of a patent.

The following definitions and non-limiting guidelines must be considered in reviewing the description of this invention set forth herein.

The headings (such as "Introduction" and "Summary,") and sub-headings (such as "Surgical Methods") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating the embodiment of the invention, are intended for purposes of illustration only and are not intended to limit the scope of the invention. Moreover, recitation of multiple embodiments having stated features is not intended to exclude other embodiments having additional features, or other embodiments incorporating different combinations stated of the features.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include" and its variants is intended to be non-limiting, such that recitation of items in a list is not to the exclusion of other like items that may also be useful in the materials, compositions, devices, and methods of this invention.

Materials

An embodiment of this invention consists of 3 parts. FIG. 1. The first part is a flexible graft 11. The graft 11 measures from about 2 to 8 mm in diameter. In a preferred embodiment, the diameter is about from 6 to 8 mm. In general, graft lengths range from 20 to 60 cm in length. Preferably, the graft is about 40 cm in length. The diameter and length of the graft depends on whether insertion is through an upper or lower extremity and the patient's body size. A graft placed in the lower extremity will be longer than a graft placed in the upper extremity. For example, the graft dimensions in a child with a graft in the upper extremity will be of smaller dimensions than those in an adult with a graft in the lower extremity. The flexible material is biocompatible and does not substantially adversely affect the function, growth and any other desired characteristics of the tissue cells surrounding the implanted device. In a preferred embodiment, the graft is made of polytetrafluoroethylene (PTFE) or polyurethane (Vectra® Graft by Thoratec).

The second part consists of a single lumen venous outflow catheter 12. The venous outflow catheter 12 has a smaller diameter than the PTFE graft 11. In a most preferred embodiment, the catheter is 1 mm smaller in diameter than the graft. Venous outflow catheters have a diameter from about 1 to 7 mm. Preferably, the catheter diameter is 5 mm. The catheter diameter should be sufficient to allow for the proper fit of the catheter in the cuff 13. Similar to the graft size, the catheter size will vary depending on the age and/or body size of the patient. The catheter length can range from 20 to about 80 cm. A preferred length is from about 40 to about 60 cm. The length of the catheter must be sufficient to advance through the vein into the right atrium. The catheter is polyurethane, silicone or other biocompatible materials can be used.

The single lumen venous outflow catheter is connected to the graft by surgical anastomosis over a cuff 13. The cuff inlet is connected to the graft 11 terminal end and the cuff outlet is connected to the venous outflow catheter 12 inlet. In a preferred embodiment, the inside diameter of the cuff is graded to compensate for the size difference between the graft and the venous outflow catheter. The cuff is preferably Teflon® or Dacron®.

The total length and various diameters of shunt components will vary depending on the size of the patient, the vein or artery used and the extremity length of the patient. The shunt 10 is placed under the skin-via strict sterile surgical technique and connected to the artery (brachial, axillary, femoral or external iliac) via careful anastomosis. The shunt can be used for extracorporeal vascular access 21 through the graft. For example, hemodialysis is performed by using dialysis cannulas temporarily placed into the graft in a sterile fashion.

Embodiments of this invention begin in the artery and have a final deposit site in the right atrium. In addition to being an arteriovenous shunt due to the path between the artery and vein, embodiments of this invention are "arterioatrial" due to the path created between the artery and the right atrium. The term "arterioatrial" is not limiting to the path or methods of creating a path, but is used as a supplemental explanation and description of embodiments of this invention. This connection eliminates the need for anastomosis to a vein and thus eliminates the frequent problems that exist when a high flow system transmits into a vein such as venous aneurysms in AV fistulas and neointimal hyperplasia in AV grafts.

Methods of Use

Surgical Methods

The surgical technique for these procedures is best suited for a vascular surgical text or journal. (Benedetii, E.; DeiPino, A; Cintron J., Duarle, B., "A New Method of Creating an Arteriovenous Graft Access", Am. /. Surg., Vol. 171, No. 3, March 1996, pp. 369-370.) It is understood that one skilled in the art would recognize modifications needed to surgical procedures depending on the dimensions of the graft and individual patient needs.

The arteriovenous shunt is inserted into the patient subcutaneously using open surgical methods. The PTFE graft is anastomosed to an artery and the cuff is attached to the terminal end of the graft. The intake end of the venous outflow catheter is attached to the Teflon or Dacron cuff. A vein is "cut down" and a glide wire is inserted into the vein. The length of the glide wire required to reach the right atrium is used to determine the appropriate length of the catheter. The catheter is passed over the glide wire through the vein into the right atrium. A purse string stitch is then used to close the opening of the vein around the catheter and prevent bleeding from the vein "cut down" site.

Purified Blood Flow in a Functioning Shunt

Figure 2:
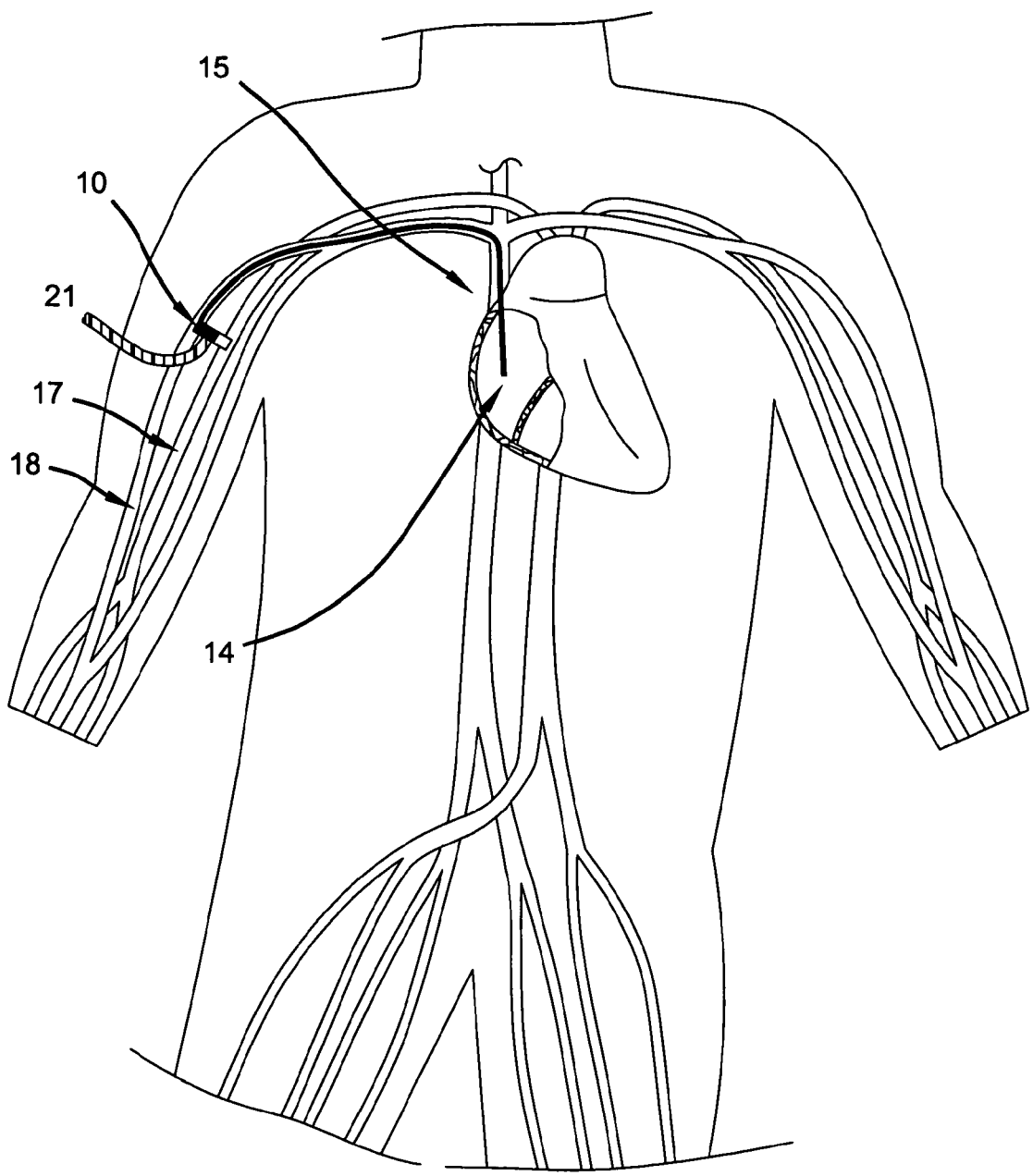
FIG. 2 depicts an arteriovenous shunt of the present invention in an upper extremity.

FIG. 2 demonstrates purified blood flow from an extracorporeal source 21, such as a hemodialysis apparatus in embodiments of an arteriovenous shunt 10 functioning in the upper extremity. As depicted, the graft is anastomosed to the brachial artery 17. The graft can also be anastomosed to the axillary artery. Blood flows from the high pressure brachial artery into the flexible graft of the shunt 10. The graft is accessed by the dialysis cannula closest to the artery in the usual sterile fashion. The blood is then filtered through a dialysis machine, the toxins removed, and the purified blood is returned to the flexible graft via the other dialysis cannula closest to the cuff. The purified blood then flows via the venous outflow catheter through the cephalic vein 18 and deposits directly into the right atrium 14. In another preferred embodiment, the catheter passes through the axillary vein. A key advantage of embodiments of this invention is the complete avoidance of stenosis which contributes to the 80% failure rate of various vascular access methods. The high pressure blood returning from the hemodialysis apparatus is guided directly into the right atrium and all vein wall contact is avoided.

Figure 3:
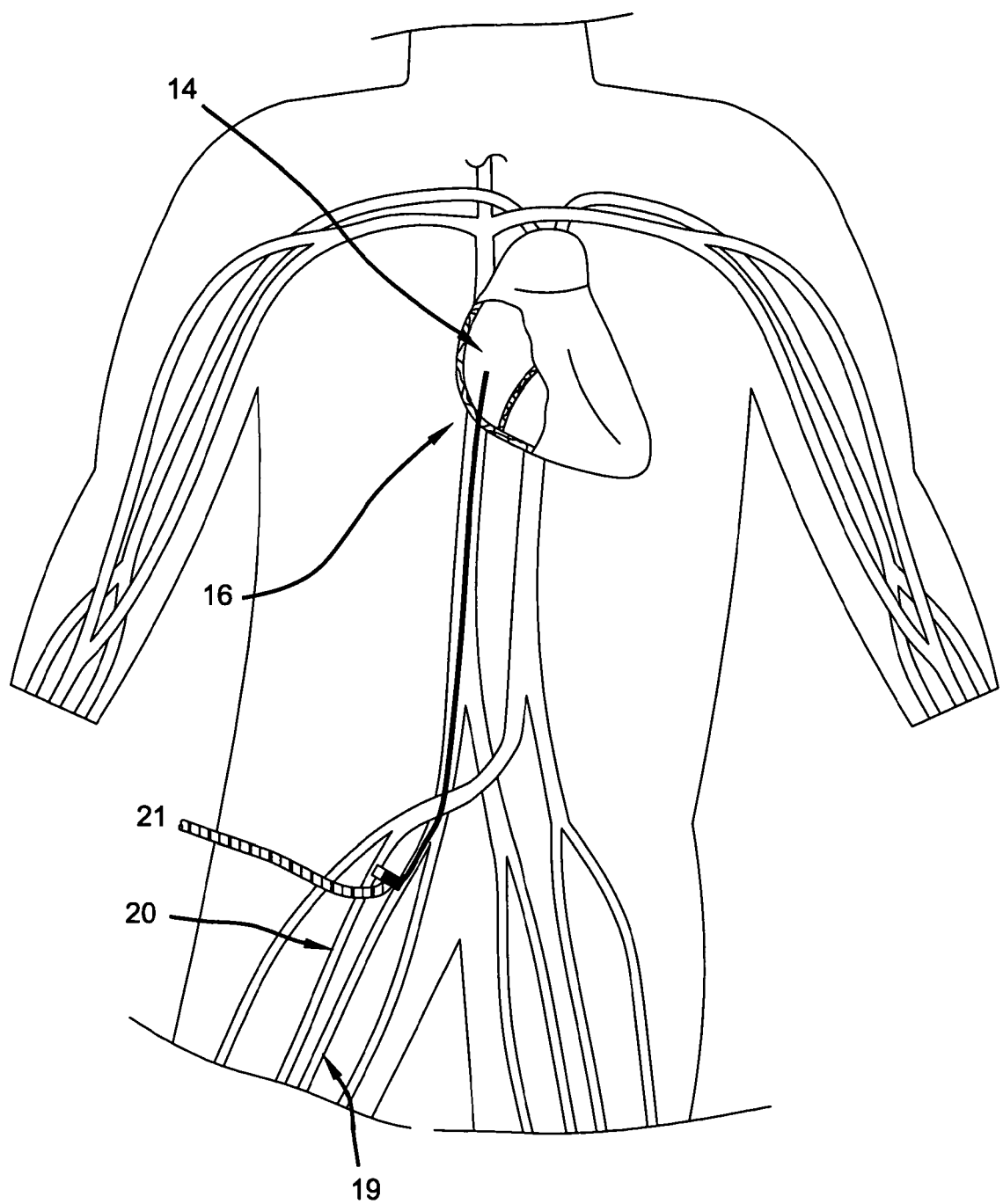
FIG. 3 depicts an arteriovenous shunt of the present in a lower extremity.

FIG. 3 depicts purified blood flow in an embodiment of the shunt functioning in the lower extremity. The graft is anastomosed to the femoral artery. Blood flows from the high pressure femoral artery 20 into the graft portion of the shunt 10. The graft is accessed in the usual sterile fashion, by the dialysis cannula closest to the artery. The blood is then filtered through the dialysis machine, the toxins removed, and the purified blood is returned to the graft via the other dialysis cannula closest to the cuff. The purified blood then flows via the venous outflow catheter through the femoral vein 19. In addition to the femoral vein, external iliac vein is also preferred. Blood then flows into the inferior vena cava 16 and deposits directly into the right atrium 14.

A key advantage of embodiments of this invention is the elimination of vein wall damage, including stenosis, which normally causes the high failure rate of various vascular access methods. The high pressure blood returning from the hemodialysis apparatus is guided directly into the right atrium and therefore venous contact with the reentering blood is avoided.

Methods of Performing Hemodialysis

Embodiments of this invention include methods of performing hemodialysis on a patient. Blood is removed from the patient through the subcutaneous graft and is passed through the hemodialysis apparatus for purification. Purified blood is collected from the hemodialysis apparatus and then transferred to the cuff and then to the venous outflow catheter. The purified blood is then transferred through the catheter which passes through the vein into the patient's right atrium. The high flow system controlled by the hemodialysis apparatus is maintained directly to the right atrium.

While specific embodiments have been illustrated and described, numerous modifications come to mind without significantly departing from the spirit of the invention and the scope of protection is limited by the scope of the accompanying claims.

What is claimed is:

1. An arteriovenous shunt comprising:
   a. an arterial graft comprising a body, a lead end and a terminal end, wherein said lead end is operable for subcutaneous connection to an artery by anastomosis and has a first diameter; and
   b. a single lumen venous outflow catheter comprising an intake end and depositing end, wherein said depositing end is operable for insertion through a vein into the right atrium of the heart and has a second diameter different from said first diameter; and
   c. a cuff comprising an inlet and an outlet, wherein:
      i. said inlet is disposed about said terminal end of said subcutaneous graft; and
      ii. said outlet is disposed about said intake end of said venous outflow catheter;
   wherein the cuff provides a secure fit for said arterial graft first diameter and said venous outflow catheter second diameter.

2. The arteriovenous shunt of claim 1 wherein said subcutaneous graft is made of a biocompatible flexible material.

3. The arteriovenous shunt of claim 2, wherein said biocompatible flexible material is epolytetrafluoroethylene (PTFE) or polyurethane.

4. The arteriovenous shunt of claim 1, wherein said arterial graft has a diameter from about 2 mm to about 8 mm and a length from about 20 cm to about 60 cm.

5. The arteriovenous shunt of claim 4, wherein said arterial graft has a diameter of from about 6 mm to about 8 mm and a length of about 40 cm.

6. The arteriovenous shunt of claim 1, wherein said artery is the brachial, axillary, femoral or external iliac artery.

7. The arteriovenous shunt of claim 1, wherein said cuff comprises polyethylene terephthalate or polytetrafluoroethylene.

8. The arteriovenous shunt of claim 1, wherein said venous outflow catheter has a diameter from about 1 mm to about 7 mm and a length of from about 20 cm to about 80 cm.

9. The arteriovenous shunt of claim 1, wherein said venous outflow catheter has a diameter from about 5 mm to about 7 mm and a length of from about 40 cm to about 60 cm.

10. The arteriovenous shunt of claim 1, wherein said venous outflow catheter is made of polyurethane or silicone.

11. The arteriovenous shunt of claim 1, wherein said vein is the cephalic, axillary, jugular, femoral or external iliac vein.

12. The arteriovenous shunt of claim 1, wherein said venous outflow catheter has a diameter of about 1 mm smaller than the subcutaneous graft.

13. A system for performing hemodialysis on a patient comprising:
   a. an arteriovenous shunt means comprising:
      i. an arterial graft means comprising a body, a lead end and a terminal end, wherein said lead end is operable for subcutaneous connection to an artery by anastomosis and has a first diameter; and
      ii. a-single lumen venous outflow catheter means comprising an intake end and depositing end, wherein said depositing end is operable for insertion through a vein into the right atrium of the heart and has a second diameter different from said first diameter; and
      iii. a cuff means comprising an inlet and an outlet, wherein:
         1. said cuff is disposed about said terminal end of said subcutaneous graft; and
         2. said cuff is disposed about said intake end of said venous outflow catheter; and
         3. wherein the cuff provides a secure fit for said arterial graft first diameter and said venous outflow catheter second diameter; and
   b. a hemodialysis apparatus.

14. The system according to claim 13, wherein said venous outflow catheter means has a diameter of about 1 mm smaller than said graft means.

15. The system according to claim 13, wherein said artery is the brachial, axillary, femoral or external iliac artery.

16. The system according to claim 13, wherein said vein is the cephalic, axillary, jugular, femoral or external iliac vein.

17. A method of performing hemodialysis on a patient comprising:
   a. inserting an arteriovenous shunt into a patient, wherein said arteriovenous shunt comprises:
      i. an arterial graft comprising a body, a lead end and a terminal end, wherein said lead end is operable for subcutaneous connection to an artery by anastomosis wherein said arterial graft has a first diameter of about 2-8 mm and length about 20 cm to 60 cm; and
      ii. a single lumen venous outflow catheter comprising an intake end and depositing end, wherein said depositing end is operable for insertion through a vein into the right atrium of the heart wherein said venous outflow catheter has a second diameter of about 1-7 mm; and a length from about 20 cm to about 80 cm;
      iii. a cuff comprising an inlet and an outlet, wherein:
         1. said inlet is disposed about said terminal end of said subcutaneous graft; and
         2. said outlet is disposed about said intake end of said venous outflow catheter;
         3. wherein the cuff provides a secure fit for said arterial graft first diameter and said venous outflow catheter second diameter; and
   b. connecting said arterial graft to a hemodialysis apparatus;
   c. collecting blood from the patient through said subcutaneous graft;
   d. passing said blood through the hemodialysis apparatus;
   e. collecting purified blood from hemodialysis apparatus; and
   f. transmitting said purified blood to the graft and then through said cuff into said venous outflow catheter to be deposited into the right atrium.

18. The method according to claim 17, wherein said venous outflow catheter has a diameter of about 1 mm smaller than said subcutaneous graft.

19. The method according to claim 17, wherein said artery is the brachial, axillary, or femoral, external iliac artery.

20. The method according to claim 17, wherein said vein is the axillary, jugular, femoral or external iliac vein.

* * * * *